United States Patent
Son et al.

(10) Patent No.: US 12,264,845 B2
(45) Date of Patent: Apr. 1, 2025

(54) STERILIZATION DEVICE

(71) Applicant: LG Electronics Inc., Seoul (KR)

(72) Inventors: Ilna Son, Seoul (KR); Bongjo Sung, Seoul (KR)

(73) Assignee: LG Electronics Inc., Seoul (KR)

( * ) Notice: Subject to any disclaimer, the term of this patent is extended or adjusted under 35 U.S.C. 154(b) by 386 days.

(21) Appl. No.: 17/911,246

(22) PCT Filed: Mar. 11, 2021

(86) PCT No.: PCT/KR2021/003006
§ 371 (c)(1),
(2) Date: Sep. 13, 2022

(87) PCT Pub. No.: WO2021/182882
PCT Pub. Date: Sep. 16, 2021

(65) Prior Publication Data
US 2023/0095203 A1    Mar. 30, 2023

(30) Foreign Application Priority Data

Mar. 13, 2020  (KR) .................. 10-2020-0031397

(51) Int. Cl.
*F24F 8/20* (2021.01)
*A61L 2/14* (2006.01)
(Continued)

(52) U.S. Cl.
CPC . *F24F 8/20* (2021.01); *F24F 8/30* (2021.01)

(58) Field of Classification Search
CPC .................. A61L 2/14; A61L 9/22; F24F 8/30
See application file for complete search history.

(56) References Cited

FOREIGN PATENT DOCUMENTS

| JP | 2002336653 | 11/2002 |
|---|---|---|
| JP | 2004351310 | 12/2004 |

(Continued)

OTHER PUBLICATIONS

English Translation of Document Identification No. WO 2004/108294 A1 provided by the World Intellectual Property Organization Website patentscope.wipo.int: Kagawa, Kenkichi; Discharge Apparatus and Air Purifying Apparatus; Dec. 16, 2004 (Year: 2004).*

*Primary Examiner* — Kevin Joyner
(74) *Attorney, Agent, or Firm* — Fish & Richardson P.C.

(57) ABSTRACT

A sterilization device includes: a frame having a first surface into which air flows, and a second surface from which air flows out; one or more discharge electrodes disposed in the frame; and a plurality of ground electrodes alternately arranged with the discharge electrodes. The discharge electrodes each comprise: a framework extending in the direction parallel to the ground electrodes; a first discharge needle protruding toward the first surface from the framework; and a second discharge needle protruding toward the second surface from the framework. The discharge electrodes are inclined at a predetermined angle with respect to an arbitrary axis of rotation parallel to the direction in which the ground electrodes extend, such that a discharge treatment region is formed perpendicularly to a flow direction by means of the alternate arrangement of the discharge electrodes and the ground electrodes parallel to the flow direction.

21 Claims, 11 Drawing Sheets

(51) Int. Cl.
*A61L 9/22* (2006.01)
*F24F 8/30* (2021.01)

(56) References Cited

FOREIGN PATENT DOCUMENTS

| | | | | |
|---|---|---|---|---|
| JP | 2006297182 | | 11/2006 | |
| KR | 100134923 | | 12/2010 | |
| KR | 20190102538 | | 9/2019 | |
| WO | WO-2004108294 A1 * | 12/2004 | ............... | A61L 9/18 |

* cited by examiner (a)

(b)

STERILIZATION DEVICE

CROSS-REFERENCE TO RELATED APPLICATIONS

This application is a National Stage application under 35 U.S.C. § 371 of International Application No. PCT/KR2021/003006, filed on Mar. 11, 2021, which claims the benefit of Korean Patent Application No. 10-2020-0031397, filed on Mar. 13, 2020. The disclosures of the prior applications are incorporated by reference in their entirety.

TECHNICAL FIELD

The present disclosure relates to a sterilization device or sterilizer, and more particularly, to an arrangement structure of a discharge electrode and a ground electrode.

BACKGROUND ART

A sterilization device or sterilizer is a device provided in an air conditioner to remove contaminants such as bacteria or odor-causing molecules in introduced air to maintain a good air quality.

The sterilization device includes a discharge electrode and a ground electrode for causing a plasma discharge when a high voltage is applied and performs sterilization using a mechanism that ionizes contaminants by the plasma discharge to remove the contaminants.

However, in the case of the conventional sterilization device, a discharge treatment or processing region is formed parallel to a flow direction, which is disadvantageous to increase a discharge processing region, thereby making it difficult to sterilize all the large amount of air introduced into an air conditioner.

In order to solve this problem, an attempt has been made to form a discharge processing region perpendicular to a flow direction. However, due to the arrangement of a discharge electrode and a ground electrode, the resistance to flowing air increases, which resulted in a decrease in performance of an air conditioner.

In addition, an electric field formed in the discharge processing region is not uniformly distributed, air introduced into a specific region is discharged without being sterilized, causing wasted power to thereby reduce the efficiency of sterilization.

DISCLOSURE OF INVENTION

Technical Problem

It is an objective of the present disclosure to provide a sterilization device that can sterilize all air flowing in an air conditioner by increasing a discharge processing region formed by a discharge electrode and a ground electrode.

It is another objective of the present disclosure to reduce the amount of air passing through a sterilization device without being sterilized by uniformly distributing an electric field produced in a discharge processing region.

It is yet another objective of the present disclosure to minimize the flow resistance caused by a structure of a sterilization device, thereby preventing a decrease in performance of an air conditioner due to a reduced flow rate of air passing through the sterilization device.

The objectives of the present disclosure are not limited to the objectives described above, and other objectives not stated herein will be clearly understood by those skilled in the art from the following description.

Technical Solution

According to an aspect of the subject matter described in this application, a sterilization device includes: a frame defining a first surface through which air is introduced and a second surface through which air is discharged; a discharge electrode disposed in the frame; a plurality of ground electrodes extending in a direction intersecting a direction from the first surface to the second surface.

The discharge electrode and the ground electrode may be alternately arranged.

The discharge electrode may include: a body extending in a direction parallel to the ground electrode; a first discharge needle protruding from the body toward the first surface; and a second discharge needle protruding from the body toward the second surface.

The discharge electrode may be inclined at a predetermined angle with respect to an arbitrary rotation axis parallel to a direction in which the ground electrode extends.

The body may have a first bending point bent toward the first surface and a second bending point bent toward the second surface.

The first discharge needle may be formed at the second bending point, and the second discharge needle may be formed at the first bending point.

An imaginary line connecting an end of the first discharge needle and the first bending point, and an imaginary line connecting an end of the second discharge needle and the second bending point may be parallel to a direction in which the body extends.

The body, the first discharge needle, and the second discharge needle may be located on a same plane.

A minimum distance between an end of the first discharge needle and the ground electrode may be equal to a minimum distance between an end of the second discharge needle and the ground electrode.

An inclined angle of the discharge electrode may be in a range of 10° to 20°.

A minimum distance between an end of the first discharge needle and the ground electrode, and a minimum distance between an end of the second discharge needle and the ground electrode may be in a range of 4 mm to 9 mm.

The frame may include a partition wall by which an inside thereof is divided into a first sterilization region and a second sterilization region.

The discharge electrode and the ground electrode may be distributed and disposed in the first sterilization region and the second sterilization region.

The first sterilization region and the second sterilization region may be symmetrical with respect to the partition wall.

The discharge electrode disposed above a center line of the first surface and the second surface may be inclined downward toward the second surface, and the discharge electrode disposed below the center line of the first surface and the second surface may be inclined upward toward the second surface.

Any one of a high voltage wire for applying a high voltage to the discharge electrode and a ground wire for connecting the ground electrode may be disposed in the partition wall.

The frame may be installed on a flow path through which air flows.

The ground electrode may extend in a direction intersecting a flow direction of the air.

The first discharge needle may protrude from the body to an upstream side of the flow direction of the air.

The second discharge needle may protrude from the body to a downstream side of the flow direction of the air.

Details of other embodiments are included in the detailed description and the accompanying drawings.

Advantageous Effects

A sterilization device according to the present disclosure has one or more of the following effects.

First, a discharge processing region may be formed perpendicular to a flow direction by the alternating arrangement of discharge and ground electrodes parallel to the flow direction, allowing all air passing through a sterilization device to be sterilized, and the sterilization device to have a wider discharge processing region while achieving a compact design within a frame.

Second, a discharge electrode forming a predetermined angle with respect to a flow direction may be disposed to facilitate the formation of a streamer discharge occurring between the discharge electrode and a ground electrode. Accordingly, a discharge processing region formed in a sterilization device may be maximized to thereby reduce wasted power consumption and improve the sterilization efficiency.

Third, by adjusting the range of an angle formed by a discharge electrode with a flow direction, the flow resistance to flowing air may be minimized, allowing the formation of a streamer discharge to be selectively facilitated without reducing air blowing performance of an air conditioner.

The effects of the present disclosure are not limited to the effects described above, and other effects not mentioned will be clearly understood by those skilled in the art from the claims.

Figure 5:
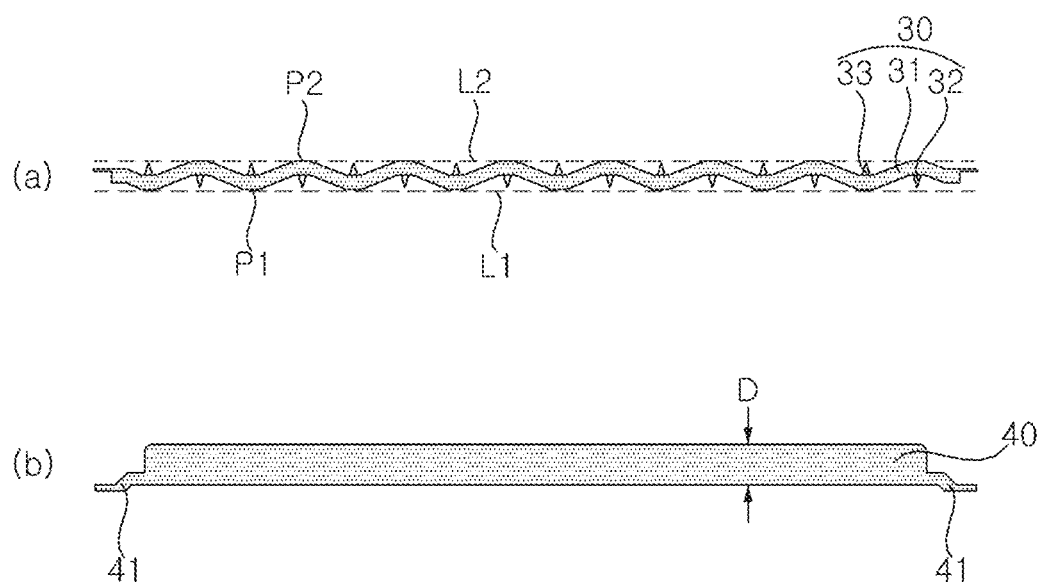

(a) of FIG. 5 is a top view of a discharge electrode according to an embodiment of the present disclosure.

(b) of FIG. 5 is a top view of a ground electrode according to an embodiment of the present disclosure.

Figure 6:
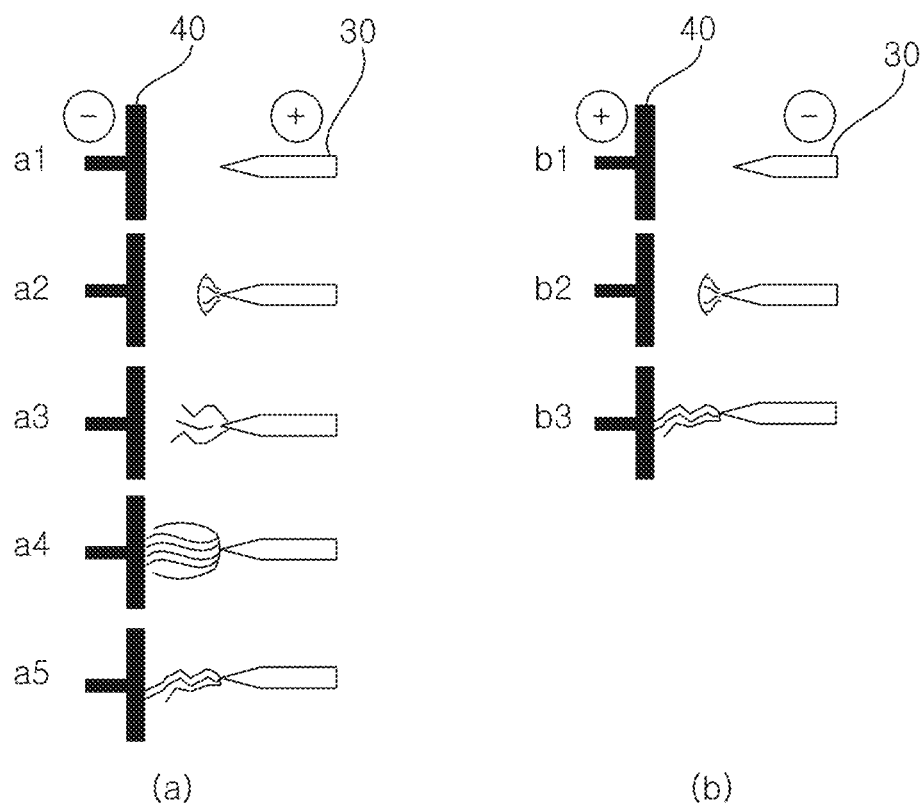

FIG. 6 is a conceptual view showing types of plasma discharge, (a) of FIG. 6 illustrates an example in which a positive voltage is applied to a discharge electrode, and (b) of FIG. 6 illustrates an example in which a negative voltage is applied to the discharge electrode.

Figure 7:
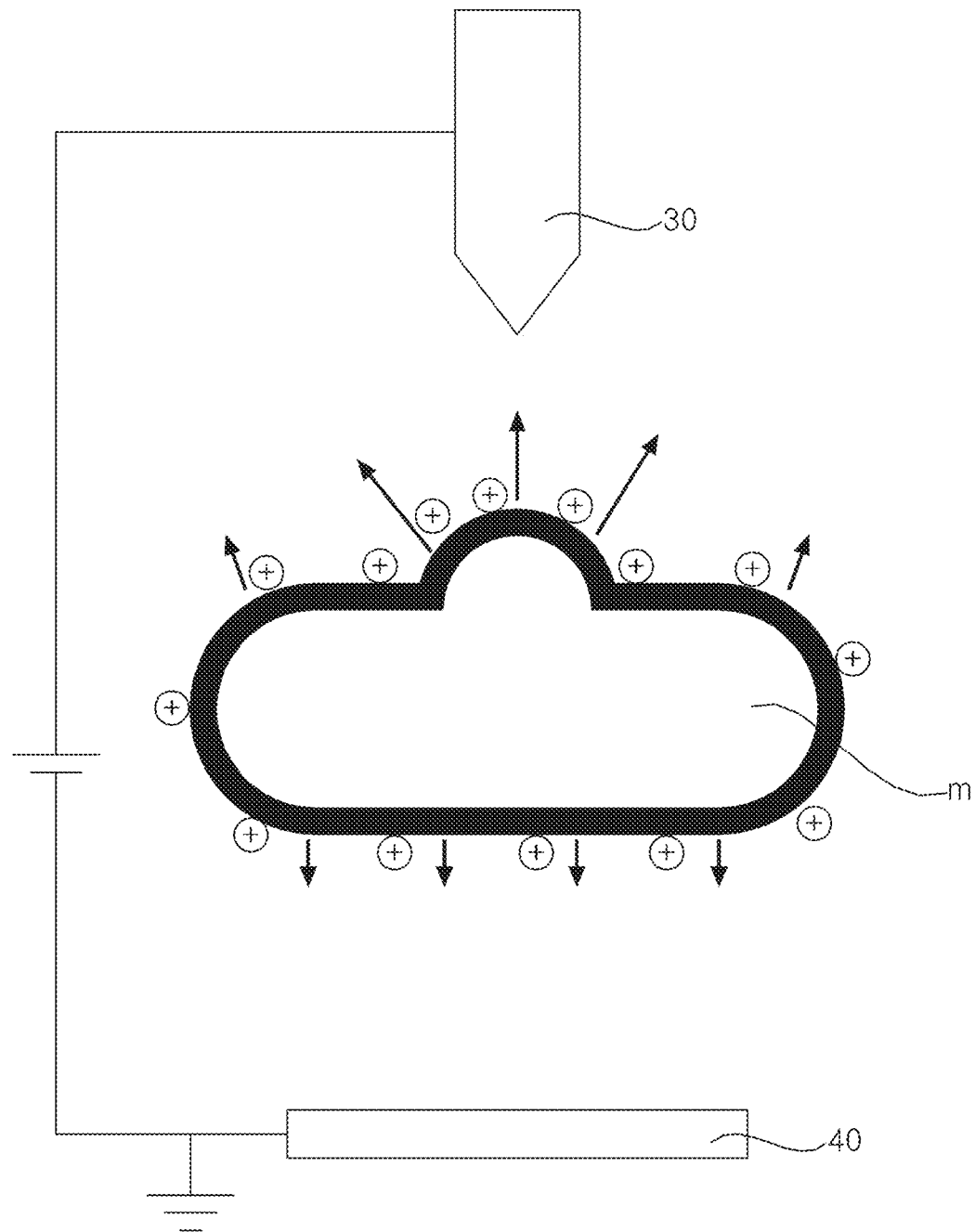

FIG. 7 is a conceptual view illustrating the principle of sterilization of air passing through a plasma discharge region.

Figure 3:
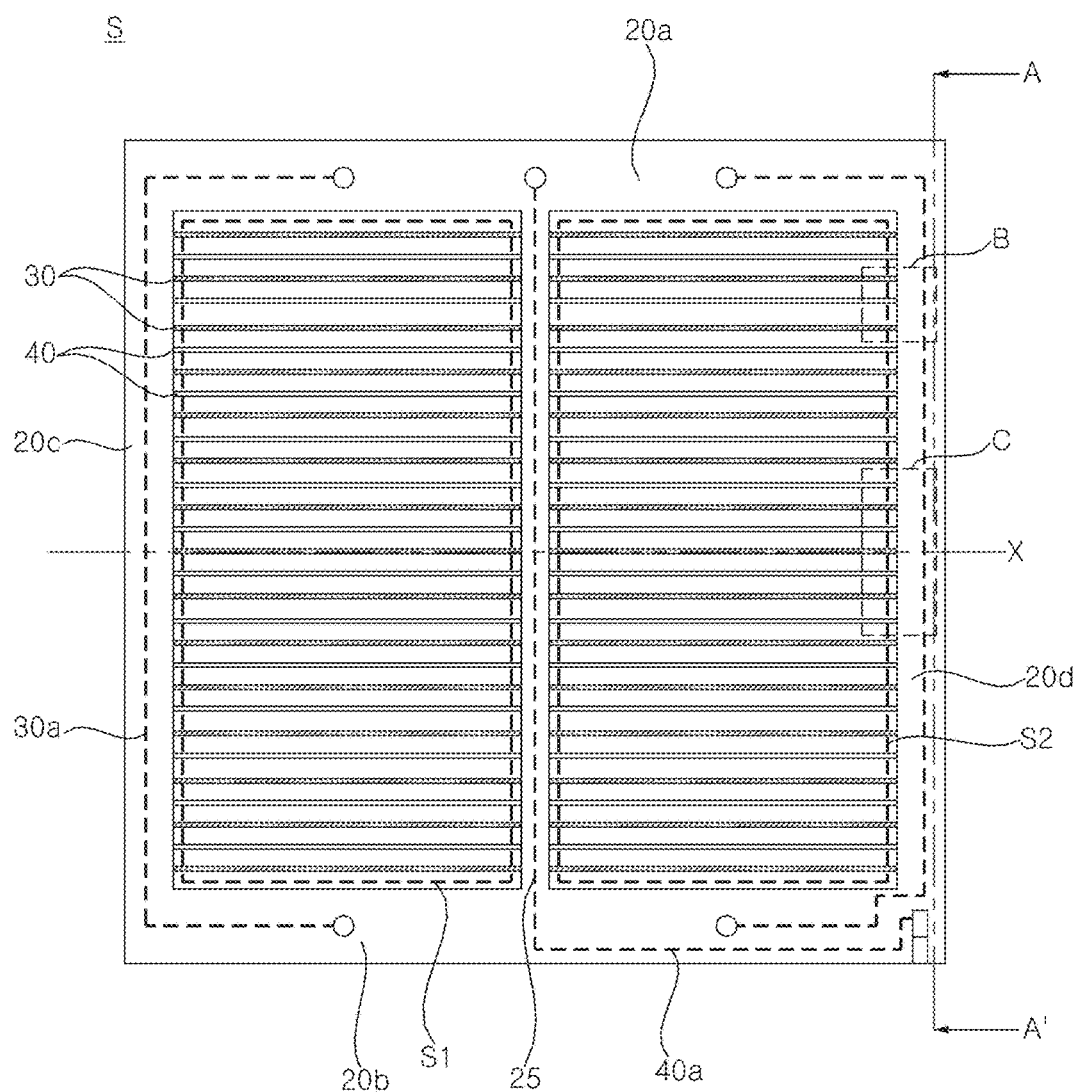
FIG. 3 is a front view of a sterilization device according to an embodiment of the present disclosure.
Figure 8:
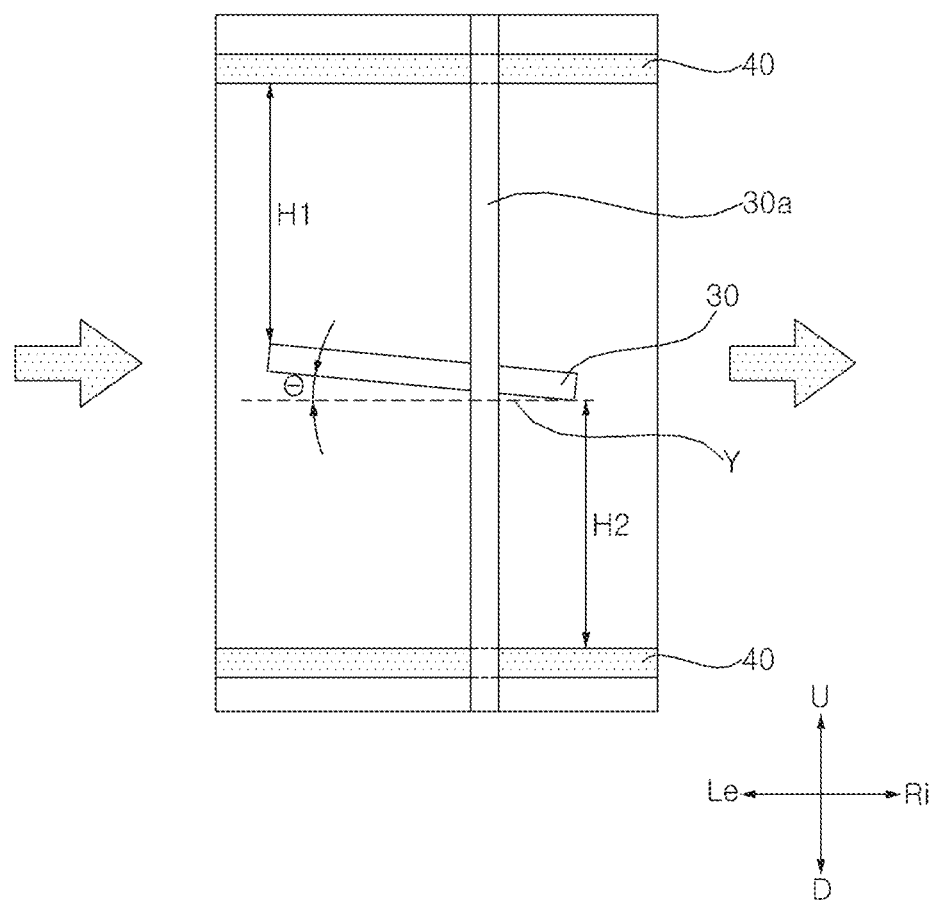

FIG. 8 is a side view of a portion B of a sterilization device according to an embodiment of the present disclosure cut in a direction A-A' in FIG. 3.

Figure 9:
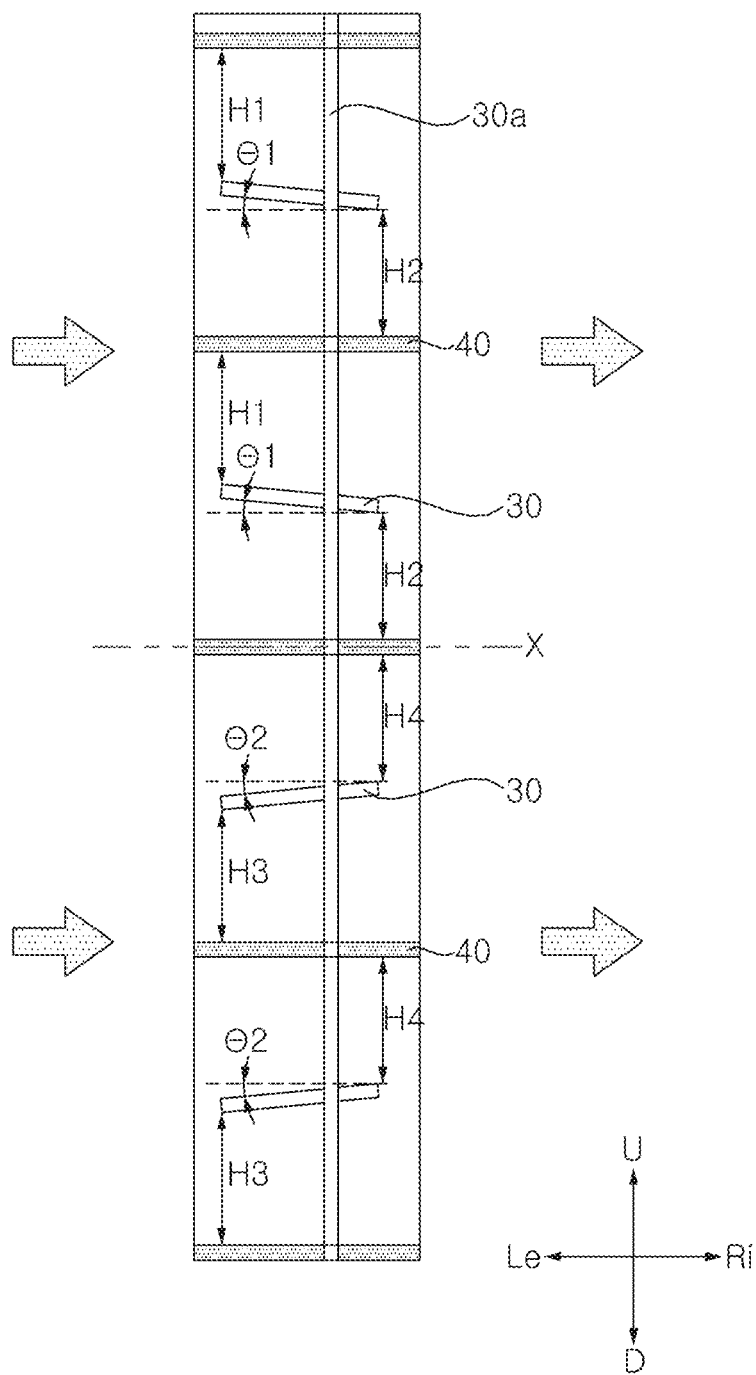

FIG. 9 is a side view of a portion C of a sterilization device according to an embodiment of the present disclosure cut in a direction A-A' in FIG. 3.

Figure 10:
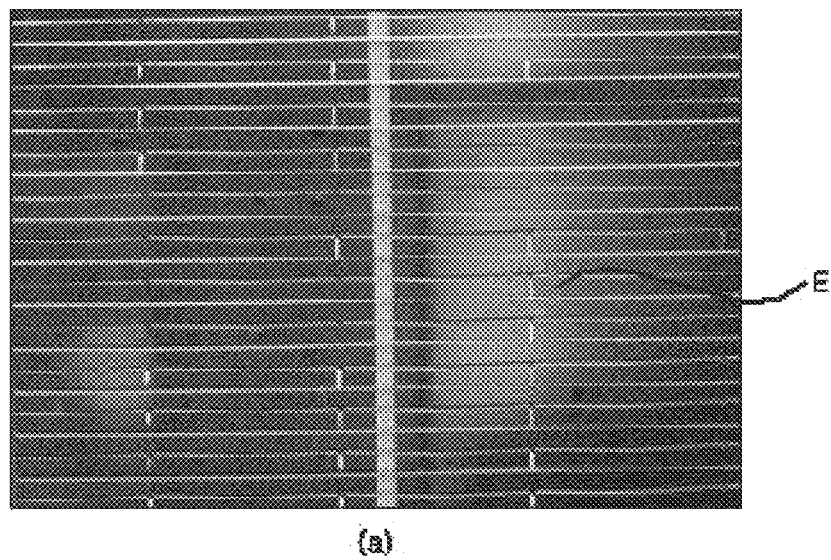
Figure 10:
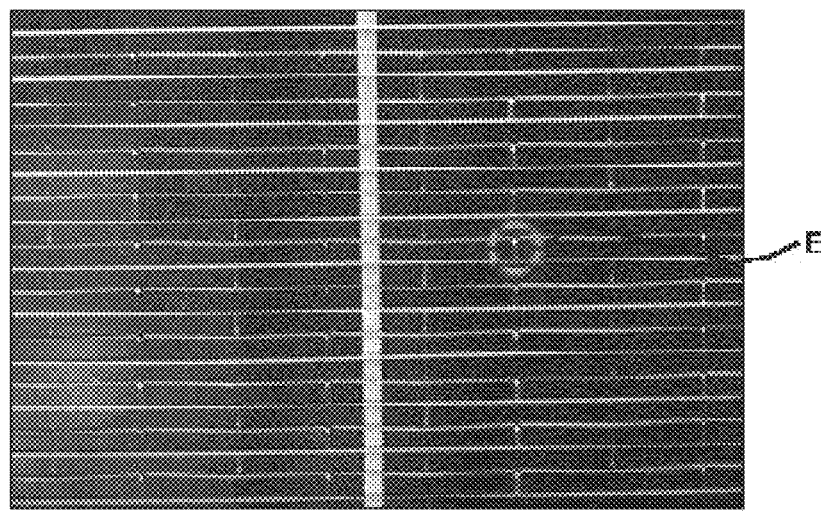

FIG. 10 shows comparison of the efficiency of a sterilization device between the present disclosure and the related art, (a) of FIG. 10 shows the discharge phenomenon of a sterilization device according to the related art, and (b) of FIG. 10 shows the discharge phenomenon of a sterilization device according to an embodiment of the present disclosure.

Figure 11:
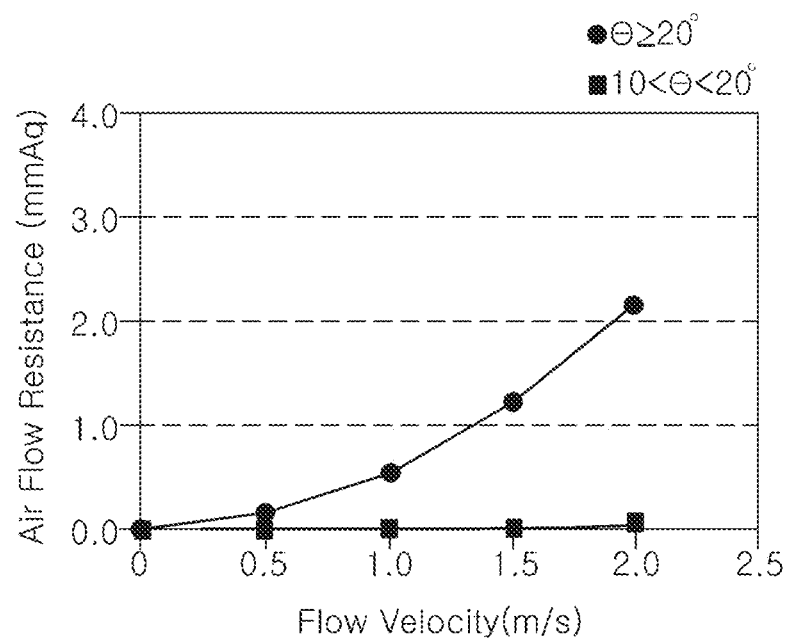

FIG. 11 is a graph showing the magnitude of airflow resistance according to a slope of a discharge electrode.

MODE FOR INVENTION

The above and other aspects, features and other advantages of the present disclosure will be more clearly understood from the following detailed description taken in conjunction with the accompanying drawings. Exemplary embodiments will now be described more fully hereinafter with reference to the accompanying drawings; however, they may be embodied in many different forms and should not be construed as limited to the embodiments set forth herein. Rather, these embodiments are provided so that this disclosure will be thorough and complete, and will fully convey the scope of the exemplary embodiments to those skilled in the art. The same reference numerals are used throughout the drawings to designate the same or similar components.

Hereinafter, a sterilization device according to embodiments of the present disclosure will be described with reference to the accompanying drawings.

Figure 1:
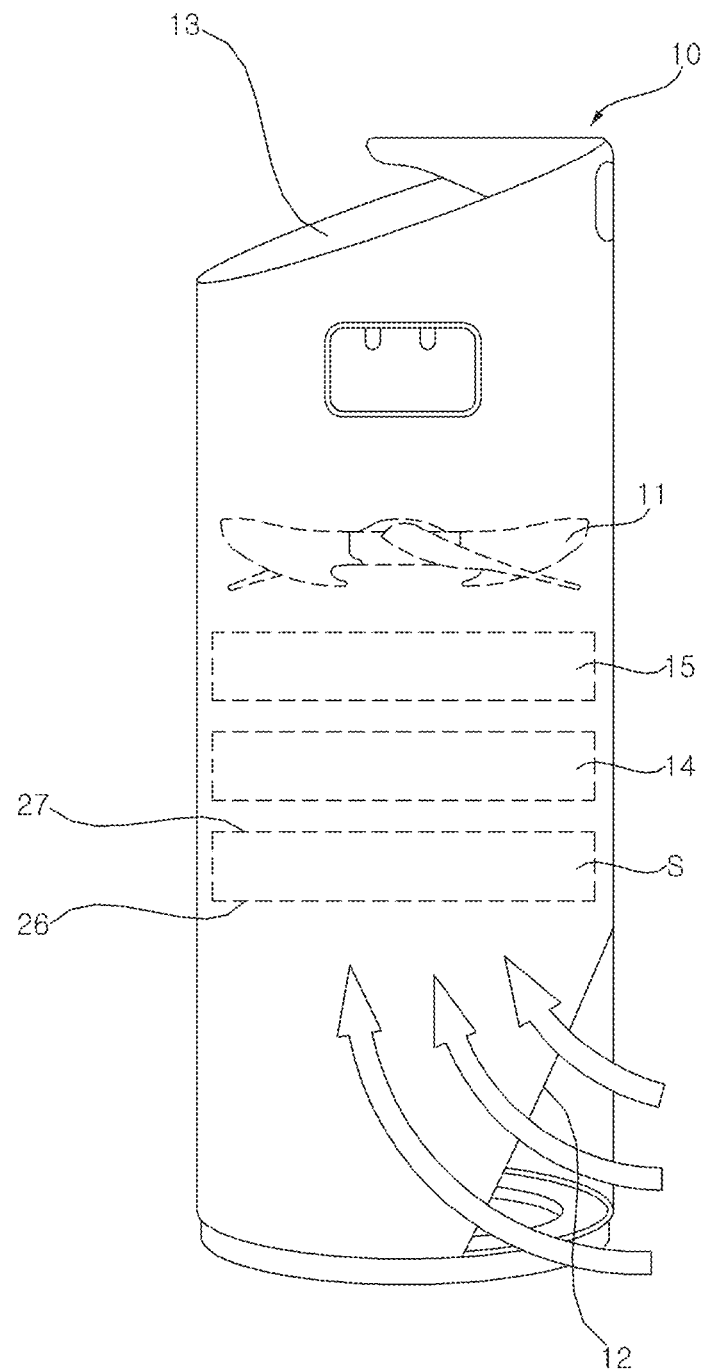
FIG. 1 is a schematic view showing an internal configuration of an air conditioner according to an embodiment of the present disclosure.

Referring to FIG. 1, an air conditioner 10 to which an embodiment of the present disclosure is applied may include a main body with a cylindrical shape, an inlet 12 provided at a lower portion of the main body to suck air, an outlet 13 provided at an upper portion of the main body to discharge air sucked into the inlet 12, a blower fan 11 provided in the main body to allow air to flow from the inlet 12 to the outlet 13, and a sterilization device S that uses a plasma discharge to sterilize air sucked in.

The air conditioner 10 may be configured such that the inlet 12 through which air is sucked is provided at a lower side of the sterilization device S, and the outlet 13 through which air is discharged to the outside is provided at an upper side of the sterilization device S.

In addition, the blower fan 11 that causes air to flow to the upper side of the sterilization device S may be provided. In this case, the outlet 13 may be formed at an upper side of the blower fan 11. That is, the blower fan 11 may be disposed between the sterilization device S and the outlet 13.

The shape of the air conditioner 10 shown in FIG. 1 is for illustration only, and the present disclosure is not limited thereto.

Meanwhile, a motor (not shown) that operates the blower fan 11, various circuit components, a filter, and the like may be accommodated in the main body of the air conditioner 10. The blower fan 11 may perform the function of sucking in polluted air from the outside and discharging purified air back to the outside.

The blower fan 11 may be provided at the upper side of the sterilization device S to cause air to flow from the lower side of the sterilization device S to the upper side of the sterilization device S. Accordingly, air may sequentially flow through the inlet 12, the sterilization device S, and the outlet 13. In addition, various filters may be disposed between the inlet 12 and the blower fan 11.

The sterilization device S may be disposed in the main body to sterilize and purify air sucked through the inlet 12. A periphery of the sterilization device S may have the same shape as an inner periphery of the main body.

The air conditioner 10 may include a dust collector 14 that collects foreign substances contained in air, and a heat exchanger 15. The sterilization device S, the dust collector 14, the heat exchanger 15, and the blower fan 11 may be sequentially installed at the air conditioner in a direction from the inlet 12 to the outlet 13.

The sterilization device S may have a square loop shape (see FIGS. 2 and 3), and may be provided with a first surface 26 through which air is introduced therein along an air flow direction in the air conditioner 10, and a second surface 27 through which air is discharged therefrom.

The first surface 26 may be disposed to face a lower part of the main body inside the air conditioner 10, and the second surface 27 may be disposed to face an upper part of the main body inside the air conditioner 10.

The detailed structure and arrangement of the first surface 26 and the second surface 27 will be described later.

Hereinafter, the overall configuration of the sterilization device S according to an embodiment of the present disclosure will be described with reference to FIGS. 2 and 3.

An overall shape of the sterilization device S may be defined by a frame 20.

The frame 20 may have a rectangular closed loop shape, and may define a space in which a discharge electrode 30 and a ground electrode 40 are disposed.

The frame 20 may be a coupled assembly of a front body 21 and a rear body 22. The front body 21 and the rear body 22 may have the same shape, and may be attached to each other to form the frame 20.

Openings, which have the same area, may be formed in the front body 21 and the rear body 22, respectively, and air may be introduced and discharged through the openings.

Air may be introduced through a front surface of the front body 21, and may then be discharged through a rear surface of the rear body 22. Accordingly, an opening formed by the front surface of the front body 21 may be defined as the first surface 26, and an opening formed by the rear surface of the rear body 22 may be defined as the second surface 27.

Air may flow from the first surface 26 to the second surface 27, and may flow through a space between the discharge electrode 30 and the ground electrode 40.

The frame 20 may have a rectangular closed loop shape, and thus, the frame 20 may be divided into an upper frame 20a located at an upper side thereof, a lower frame 20b located at a lower side thereof, and a first side frame 20c and a second side frame 20d located at left and right sides thereof, respectively.

However, the division of the frame 20 into sub-components 20a, 20b, 20c, and 20 is only for the convenience of description, and the sub-components do not limit the scope of the claims.

A partition wall 25 may be formed at a center of the frame 20, and the partition wall 25 may extend from the upper frame 20a to the lower frame 20b.

The partition wall 25 may extend perpendicular to both the upper frame 20a and the lower frame 20b, and a distance from the partition wall 25 to the first side frame 20c may be equal to a distance from the partition wall 25 to the second side frame 20d.

In addition, the partition wall 25 may be disposed parallel to the side frames 20c and 20d.

The partition wall may divide an inner space of the frame 20 into a first sterilization region S1 formed on the left with respect to FIG. 3 and a second sterilization region S2 formed on the right with respect to FIG. 3.

The first sterilization region S1 and the second sterilization region S2 may have the same volume, and the discharge electrode 30 and the ground electrode 40 may be distributed and disposed in the first sterilization region S1 and the second sterilization region S2.

The discharge electrode 30 and the ground electrode 40 may be disposed to be symmetrical with respect to the partition wall 25. In other words, the first sterilization region S1 and the second sterilization region S2 may be symmetrical to each other with respect to the partition wall 25.

The ground electrode 40 may extend in a direction perpendicular to the partition wall 25 and the side panels 20c and 20d, and both ends of a ground electrode disposed in the first sterilization region S1 may be in contact with a first side panel 20c and the partition wall 25, respectively, and both ends of a ground electrode disposed in the second sterilization region S2 may be in contact with a second side panel 20d and the partition wall 25, respectively.

The ground electrode 40 may have a flat plate shape, and the ground electrode 40 may be disposed parallel to the upper and lower frames 20a and 20b.

A plurality of ground electrodes 40 may be disposed to be spaced apart from one another, and the plurality of ground electrodes 40 may be spaced at equal intervals or distances.

A plurality of discharge electrodes 30 may be disposed between the plurality of ground electrodes 40, and the plurality of discharge electrodes 30 may be spaced at equal intervals or distances.

In addition, the discharge electrode 30 may have a flat plate shape, and may be disposed parallel to the upper and lower frames 20a and 20b.

The discharge electrode 30 and the ground electrode 40 may be disposed in parallel with each other. In other words, the discharge electrode 30 and the ground electrode 40 may have a length that extends in a direction intersecting a direction from the first surface 26 to the second surface 27.

The ground electrode 40 may be connected to a ground wire 40a disposed in the frame 20, and a ground terminal groove 21a to which the ground wire 40a is connected may be formed on a lower right end portion of the front body 21.

The discharge electrode 30 may be connected to a high voltage wire 30a disposed in the frame 20, and a high voltage terminal groove 22a to which the high voltage wire 30a is connected may be formed on an upper left end portion of the rear body 22.

The sterilization device S may apply a high voltage, through the high voltage terminal groove 22a, from a high voltage supplier (not shown) to the discharge electrode 30 through the high voltage wire 30a.

The high voltage wire 30a and the ground wire 40a may be a conductor made of a conductive material capable of applying a voltage, not being limited to a wire.

A gap generated when the front body 21 and the rear body 22 are coupled to each other may be formed in the side panel 20c, 20d, and the discharge electrode 30 may be brought into contact with the high voltage wire 30a disposed in the side panel 20c, 20d through the gap.

The ground wire 40a may be disposed in the partition wall 25, and a portion of the ground electrode 40 may be inserted into the partition wall 25 to be in contact with the ground wire 40a.

The ground wire 40a may be disposed vertically in the partition wall 25, and a lower part of the ground wire 40a may extend through an inside of the lower frame 20b to ground a circuit formed in the sterilization device S through the ground terminal 21a.

The high voltage wire 30a may be disposed in each of the side frames 20c and 20d, and may be disposed vertically to be connected to all the discharge electrodes 30 disposed in the first sterilization region S1 and the second sterilization region S2.

A first through-hole 23 and a second through-hole 24, which have a shared opening region, may be formed in the front body 21 and the rear body 22.

Four first through-holes 23 may be formed on upper and lower sides of the first and second sterilization regions S1 and S2, the frame 20 may be fastened to the air conditioner 10 through a fastening member (not shown) that passes through the first through-hole 23, and the high voltage wire 30a may be drawn in the frame 20 through the first through-hole 23.

The second through-hole 24 may be formed on an upper side of the partition wall 25, the frame 20 may be connected to the air conditioner 10 through a fastening member (not shown) that passes through the second through-hole 24, and the ground wire 40a may be drawn in the frame 20 through the second through-hole 24.

Hereinafter, the structure and arrangement relations of the discharge electrode 30 and the ground electrode 40 will be described with reference to FIGS. 4 and 5.

Figure 2:
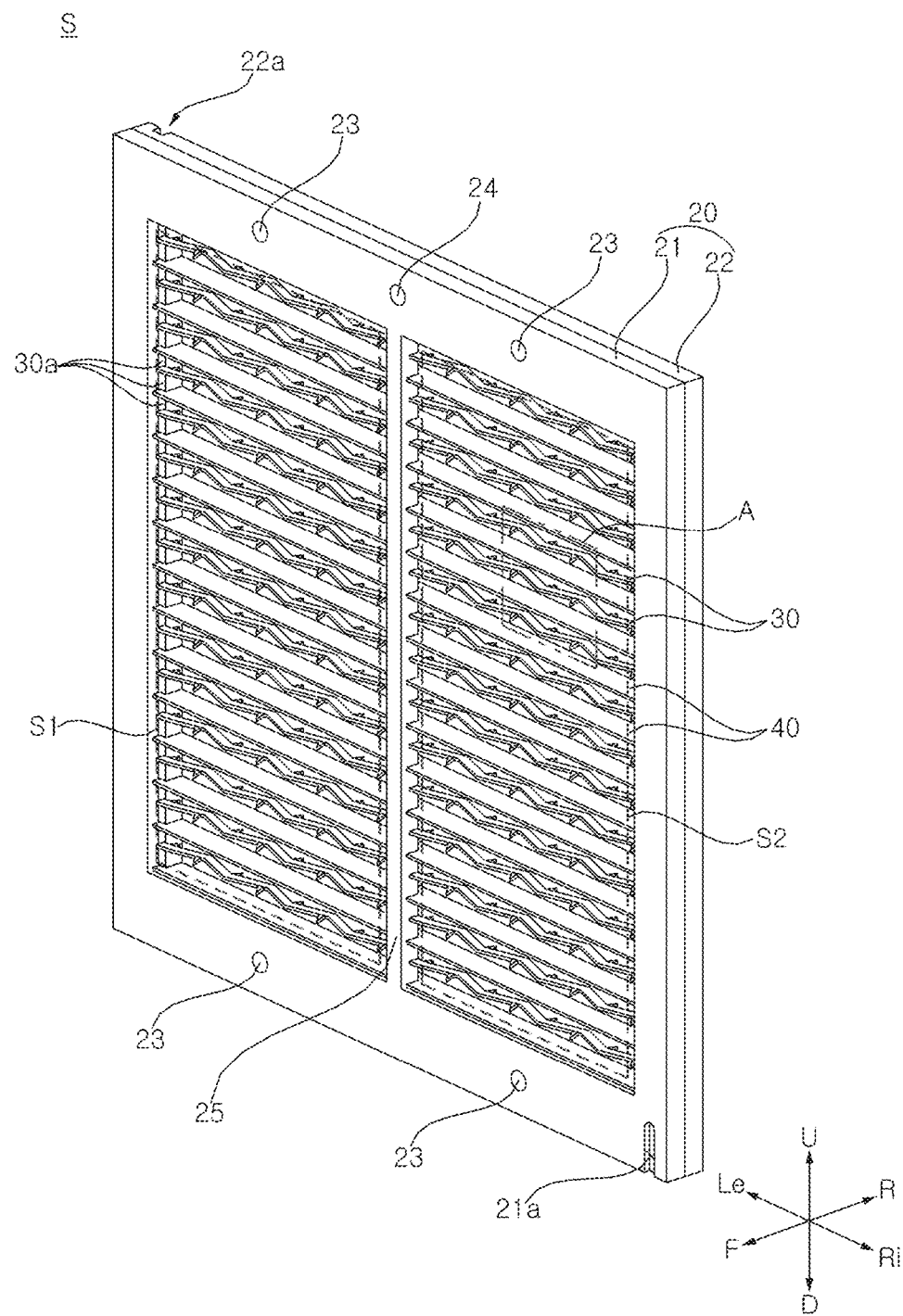
FIG. 2 is a perspective view of a sterilization device according to an embodiment of the present disclosure.
Figure 4:
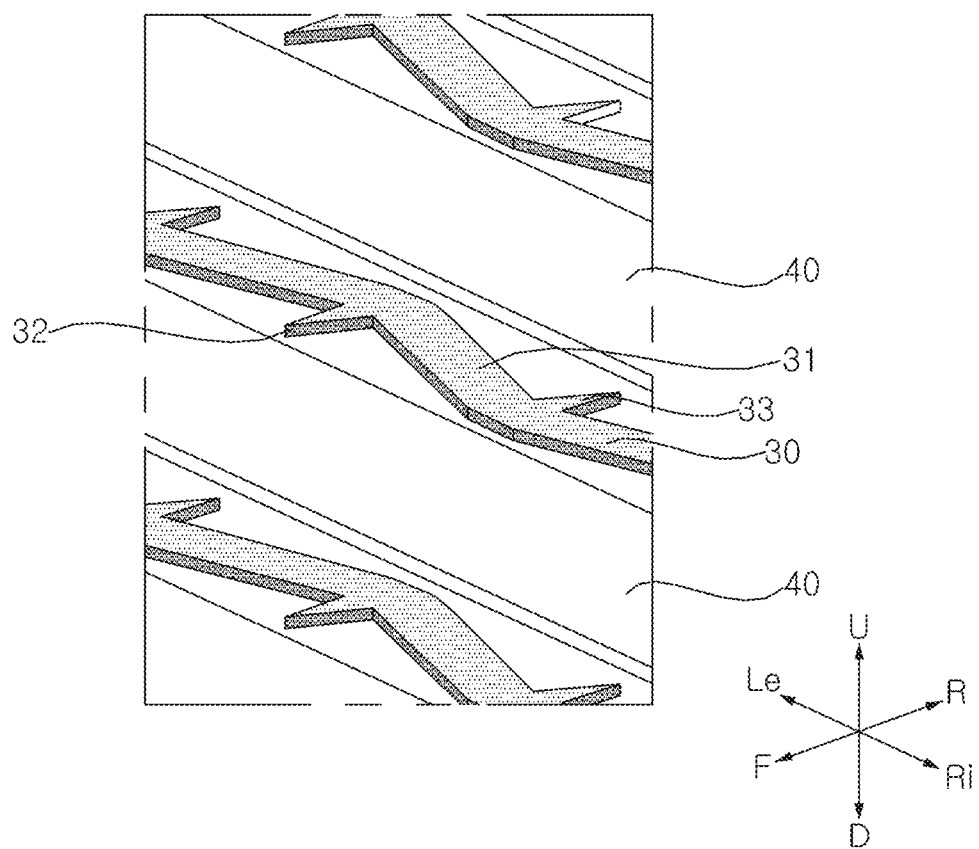
FIG. 4 is an enlarged view of a portion A in FIG. 2.

FIG. 4 is an enlarged view of a portion A in FIG. 2, and FIG. 5 shows the discharge electrode 30 and the ground electrode 40 viewed from above.

The discharge electrode 30 and the ground electrode 40 may each be provided in plurality, and the plurality of discharge electrodes 30 and the plurality of ground electrodes 40 may be alternately arranged. Accordingly, the plurality of discharge electrodes 30 and the plurality of ground electrodes 40 may be alternately arranged in the up-and-down direction.

The plurality of discharge electrodes 30 may be spaced at equal intervals, and the plurality of ground electrodes 40 may be spaced at equal intervals.

The ground electrode 40 may have a flat plate shape, and a contact portion 41 in contact with the ground wire 40a may be formed at each of both ends of the ground electrode 40.

The discharge electrode 30 may include a framework or body 31 that defines an overall shape of the discharge electrode 30, a first discharge needle 32 that protrudes from the body 31 toward the front, and a second discharge needle 33 that protrudes from the body 31 toward the rear.

Here, since the first surface 26 formed by the frame 20 is disposed at the front of the discharge electrode 30, it may also be expressed that the first discharge needle 32 protrudes toward the first surface 26.

Likewise, since the second surface 27 formed by the frame 20 is disposed at the rear of the discharge electrode 30, it may also be expressed that the second discharge needle 33 protrudes toward the second surface 27.

The first discharge needle 32 and the second discharge needle 33 may be each be provided in plurality in a longitudinal direction of the body 31, and the plurality of first discharge needles 32 and the plurality of second discharge needles 33 may be alternately disposed along the longitudinal direction of the body 31.

The body 31, the first discharge needle 32, and the second discharge needle 33 may be disposed on the same plane. Accordingly, when the discharge electrode 30 is viewed from the side, the discharge electrode 30 may be seen as a thin plate.

The body 31 may have a zigzag shape. Here, the zigzag shape may mean a shape in which directions bent forward and backward along the longitudinal direction of the body 31 intersect each other.

The body 31 may have a plurality of bending points P1 and P2 at which an extended direction of the body 31 changes.

The bending points P1 and P2 may be classified into a first bending point P1 formed at a point bent toward the front, and a second bending point P2 formed at a point bent toward the rear.

Here, since the first surface 26 formed by the frame 20 is disposed at the front of the discharge electrode 30, it may also be expressed that the first bending point P1 protrudes toward the first surface 26.

Likewise, since the second surface 27 formed by the frame 20 is disposed at the rear of the discharge electrode 30, it may also be expressed that the second bending point P2 protrudes toward the second surface 27.

The first bending point P1 and the second bending point P2 may be alternately formed along the longitudinal direction of the body 31, and accordingly, the body 31 may have a zigzag shape in its longitudinal direction.

The plurality of first bending points P1 may be formed at equal intervals along the longitudinal direction of the body 31, and the plurality of second bending points P2 may be formed at equal intervals along the longitudinal direction of the body 31.

The first discharge needle 32 may protrude from the second bending point P2 toward the first surface 26, and the second discharge needle 33 may protrude from the first bending point P1 toward the second surface 27.

Here, the plurality of first discharge needles 32 may protrude from the respective plurality of second bending points P2 toward the first surface 26, and the plurality of second discharge needles 33 may protrude from the respective plurality of bending points P1 toward the second surface 27.

An imaginary line L1 connecting ends of the plurality of first discharge needles 32 and the plurality of first bending points P1 may be a straight line, and an imaginary line L2 connecting ends of the plurality of second discharge needles 33 and the plurality of second bending points P2 may be a straight line.

In addition, the two imaginary lines L1 and L2 may be parallel to the longitudinal direction in which the body 31 extends.

A length of the first discharge needle 32 protruding from the second bending point P2 may be equal to a length of the second discharge needle 33 protruding from the first bending point P1.

The end of the first discharge needle 32 may be located at a center of a line segment connecting two adjacent first bending points P1, and the end of the second discharge needle 33 may be located at a center of a line segment connecting two adjacent second bending points P2.

A distance from the end of the first discharge needle 32 to the second bending point P2 opposite the end of the first discharge needle 32 may be equal to a distance from the end of the second discharge needle 33 to the first bending point P1 opposite the end of the second discharge needle 33. The distances may be equal to a front-and-rear length D of the ground electrode 40.

Hereinafter, the principle of sterilizing contaminants by the sterilization device S of the present disclosure will be described with reference to FIGS. 6 and 7.

FIG. 10 is a conceptual view showing types of plasma discharge, (a) of FIG. 10 illustrates an example in which a positive voltage is applied to the discharge electrode 30, and (b) of FIG. 10 illustrates an example in which a negative voltage is applied to the discharge electrode 30. FIG. 11 is a conceptual view illustrating the principle of sterilization of air passing through a plasma discharge region.

A shape or form of a plasma discharge (or corona discharge) is changed by a potential difference applied between the discharge electrode 30 and the ground electrode 40. When a positive electrode or anode of a power source is connected to the discharge electrode 30 to increase the magnitude of an applied voltage, the discharge electrode 30 gradually changes in shape like a2, a3, a4, and a5 in (a) of FIG. 10. In (a) of FIG. 10, a2 denotes a glow discharge, a3 denotes a brush discharge, a4 denotes a streamer discharge, and a5 denotes an arc discharge.

When a negative electrode or cathode of the power source is connected to the discharge electrode 30 to increase the magnitude of an applied voltage, the discharge electrode 30 gradually changes in shape like b2 and b3 in (b) of FIG. 10. In (b) of FIG. 10, b2 denotes a glow discharge, and b3 denotes an arc discharge. Unlike the case when connecting the positive electrode of the power supply, a streamer discharge does not occur when the negative electrode of the power supply is connected to the discharge electrode 30.

A positive voltage may be applied by connecting the positive electrode of the power source to the discharge electrode 30 of the sterilization device S according to the embodiment of the present disclosure. As the positive high voltage is applied, the discharge electrode 30 may generate a streamer discharge toward the ground electrode 40. When more electric energy is applied to a glow discharge, an electron avalanche occurs, forming a streamer discharge that has a larger discharge region than the glow discharge and is advantageous for sterilization.

As a microorganism m suspended in air (airborne microorganism) that passes through the sterilization device S passes through a discharge region between the discharge electrode 30 and the ground electrode 40, an electric charge is accumulated on its cell wall. The Coulomb force of the electric charge causes the tension of the cell wall to break down, and eventually the cell wall is torn apart, making metabolism of the microorganism m impossible. Thus, the air is sterilized.

In order to measure sterilization performance of the sterilization device S according to the embodiment of the present disclosure, air was made to flow through the sterilization device S at a flow rate of 1 m/s, and the concentration of microorganisms m in an upstream region before passing through the sterilization device S and the concentration of microorganisms m in a downstream region after passing through the sterilization device S were compared. In one-pass sterilization performance measured in this way, greater than or equal to 60% effectiveness was experimentally observed. This is a similar level to one-pass sterilization performance of UVC LED, which is commonly used for sterilization. UV rays are divided, depending on the wavelength, into UVA (315 to 400 nm), UVB (280 to 315 nm), and UVC (100 to 280 nm). The UVC LED refers to an organic light-emitting diode using UVC.

The sterilization performance is also related to a time taken for air to pass through a plasma discharge region. When a flow path width of a region where a plasma discharge occurs is narrower than those of other flow paths, the flow of air becomes faster, and thus, electric charges may not be sufficiently accumulated in microorganisms.

As the discharge electrode 30 and the ground electrode 40 of the sterilization device S according to the embodiment of the present disclosure are arranged in parallel with the upper and lower frames 20a and 20b, a change in width of an air flow path may be minimized, allowing electric charges to be sufficiently accumulated in microorganisms suspended in air. As a result, the sterilization performance may be improved.

Hereinafter, an angle between the discharge electrode 30 and the ground electrode 40 will be mainly described with reference to FIG. 8.

FIG. 8 shows a portion B viewed from the side after cutting the second side frame 20d in a direction A-A' in FIG. 3. For the convenience of explanation, the directions up, down, left, and right shown in FIG. 8 are set differently from those described above.

Air flowing through the sterilization device S is introduced from the left with respect to FIG. 8 and is then discharged to the right with respect to FIG. 8. Accordingly, the first surface 26 is disposed at the left with respect to FIG. 8, and the second surface 27 is disposed at the right with respect to FIG. 8, which are apparent from the descriptions according to FIGS. 1 and 2.

In addition, the body 31, the first discharge needle 32, and the second discharge needle 33 may be disposed on the same plane, which may have a thin plate shape when viewed from the side.

As the discharge electrode 30 has the plate shape, it may be described that the first discharge needle 32 and the first bending point P1 are located at a left end of the discharge electrode 30 with respect to FIG. 8, and the second discharge needle 33 and the second bending point P2 are located at a right end of the discharge electrode 30 with respect to FIG. 8.

The high voltage wire 30a disposed in the second side frame 20d may extend in the up-and-down direction to be connected to the plurality of discharge electrodes 30 disposed in the frame 20.

Each of the plurality of ground electrodes 40 may be disposed to be perpendicular to the high voltage wire 30a, and the discharge electrode 30 may be disposed to be tilted or inclined at a predetermined angle to a direction orthogonal to the high voltage electrode 30a.

In other words, the discharge electrode 30 may be inclined at a predetermined angle with respect to an arbitrary rotation axis parallel to a direction in which the ground electrode 40 extends. Here, the rotation axis may be formed in the same direction as the directions in which the discharge electrode 30 and the ground electrode 40 extend inside the frame 20.

The discharge electrode 30 may be inclined from a reference line Y by an inclination angle θ. Here, the discharge electrode 30 may be inclined not only toward the lower right, but also toward the upper right.

The reference line Y may be parallel to the plurality of ground electrodes 40 disposed up and down, and may pass through the right end of the discharge electrode 30.

The inclination angle θ may be in the range of 10° to 20°, and may preferably be 15°. As a sufficient flow path between the ground electrode 40 and the discharge electrode 30 is secured, the flow resistance of air passing through the sterilization device S may be minimized.

A distance H1 between the left end of the discharge electrode 30 and a ground electrode 40, among the plurality of ground electrodes 40, disposed above the discharge electrode 30 may be equal to a distance H2 between the right end of the discharge electrode 30 and a ground electrode 40, among the plurality of ground electrodes 40, disposed below the discharge electrode 30 (H1=H2). Accordingly, the discharge electrode 30 may be disposed at a center of the two opposite ground electrodes 40, and a flow of air passing through the sterilization device S may be uniformly formed.

The distances H1 and H2 may be in the range of 4 mm to 9 mm. Accordingly, a sufficient flow path may be secured between the discharge electrode 30 and the ground electrode 40, allowing the flow resistance of air passing through the sterilization device S to be minimized.

FIG. 9 shows a portion C viewed from the side after cutting the second side frame 20d in a direction A-A' in FIG. 3. For the convenience of explanation, the directions in FIG. 9 are set the same as those in FIG. 8.

Air flowing through the sterilization device S is introduced from the left with respect to FIG. 9 and is then discharged to the right with respect to FIG. 9. Accordingly, the first surface 26 is disposed at the left with respect to FIG. 9, and the second surface 27 is disposed at the right with respect to FIG. 9, which are apparent from the descriptions according to FIGS. 1 and 2.

In addition, the body 31, the first discharge needle 32, and the second discharge needle 33 may be disposed on the same plane, which may have a thin plate shape when viewed from the side.

As the discharge electrode 30 has the plate shape, it may be described that the first discharge needle 32 and the first bending point P1 are located at a left end of the discharge electrode 30 with respect to FIG. 9, and the second discharge needle 33 and the second bending point P2 are located at a right end of the discharge electrode 30 with respect to FIG. 9.

The high voltage wire 30a disposed in the second side frame 20d may extend in the up-and-down direction, and may be connected to the plurality of discharge electrodes 30 disposed in the frame 20.

Each of the plurality of ground electrodes 40 may be disposed to be perpendicular to the high voltage wire 30a, and each of the plurality of discharge electrode 30 may be disposed to be tilted or inclined at a predetermined angle to a direction orthogonal to the high voltage electrode 30a.

In other words, the discharge electrode 30 may be inclined at a predetermined angle with respect to an arbitrary rotation axis parallel to a direction in which the ground electrode 40 extends. Here, the rotation axis may be formed in a direction the same as the directions in which the discharge electrode 30 and the ground electrode 40 extend inside the frame 20.

The discharge electrode 30 may be inclined from a reference line Y (see FIG. 8) by an inclination angle θ1, θ2. Here, when a discharge electrode 30 is inclined toward the lower right, the discharge electrode 30 may be inclined by a first inclination angle θ1, and when a discharge electrode 30 is inclined toward the upper right, the discharge electrode 30 may be inclined by a second inclination angle θ2.

A center line X may be understood as an imaginary line that divides the frame 20 into upper and lower regions, and the divided upper and lower regions may have the same or similar area.

The plurality of discharge electrodes 30 disposed in the frame 20 may be symmetrically arranged with respect to the center line X.

In more detail, among the plurality of discharge electrodes 30, a discharge electrode 30 located above the center line X may be inclined at the first inclination angle θ1, and a discharge electrode 30 located below the center line X may be inclined at the inclination angle θ2. Accordingly, the discharge electrode 30 located above the center line X may be inclined toward the lower right, and the discharge electrode 30 located below the center line X may be inclined toward the upper right.

This arrangement structure allows the discharge electrode 30 not only to perform the sterilization function, but also to serve as a flow guider that guides air, which is introduced through the first surface 26 and is then discharged through the second surface 27, to be concentrated to a center as the air moves from an upstream to a downstream.

The first inclination angle 61 and the second inclination angle θ2 may be the same. In this case, the two angles θ1 and θ2 may have opposite signs and the same absolute magnitude.

The first inclination angle 81 and the second inclination angle θ2 may be in the range of 10° to 20°, and may preferably be 15°.

A distance H1 between a left end of a discharge electrode 30 located above the center line X and a ground electrode 40 disposed above the discharge electrode 30 may be equal to a distance H2 between a right end of the discharge electrode 30 located above the center line X and a ground electrode 40 disposed below the discharge electrode 30 (H1=H2).

A distance H3 between a left end of a discharge electrode 30 located below the center line X and a ground electrode 40 disposed below the discharge electrode 30 may be equal to a distance H4 between a right end of the discharge electrode 30 located below the center line X and a ground electrode 40 disposed above the discharge electrode 30 (H3=H4).

Here, the distances may be equal (H1=H2=H3=H4), and may be in the range of 4 mm to 9 mm.

Hereinafter, an improved effect of the sterilization device S according to an embodiment of the present disclosure will be described with reference to FIGS. 10 and 11.

(a) of FIG. 10 shows a light-emitting region E by a streamer discharge of a sterilization device according to the related art, and (b) of FIG. 10 shows a light-emitting region by a streamer discharge of a sterilization device according to an embodiment of the present disclosure.

A light-emitting region E is generated by an electron avalanche, which occurs when a direct current voltage applied between a high voltage needle electrode and a flat electrode is gradually increased (to a threshold value) to cause dielectric breakdown of air at the tip of the needle electrode, leading to a rapid increase in the number of accelerated electrons to thereby cause a spark.

Here, an electric field in the discharge phase is formed when the electron avalanche occurs, reaching a state in which the densities of electrons and cations are almost the same. This discharge phenomenon is called a 'streamer discharge'.

Therefore, more light-emitting regions E, which are regions where sparks are generated by the electron avalanche, may indicate that the 'streamer discharge' occurs more easily, which ultimately proves more active or efficient sterilization.

As shown in FIG. 10, compared to the related art, more light-emitting regions E are formed in the sterilization device according to the embodiment of the present disclosure, and therefore, it can be said that more active or efficient sterilization is achieved. Since both are compared in a state where the same voltage is applied, the present disclosure exhibits improved sterilization efficiency compared to the related art.

FIG. 11 is a graph showing a change in air flow resistance according to a change of the inclination angle θ.

When the inclination angle θ is in the range of 10° to 20°, air flow resistance is measured to be low regardless of a change in flow velocity, whereas when the inclination angle θ exceeds 20°, it exhibits a sharp increase in air flow resistance as a change in flow velocity increases.

Accordingly, when the inclination angle θ is set in the range of 10° to 20°, flow resistance to air passing through the sterilization device S may be minimized to thereby facilitate the formation of the streamer discharge described above without affecting air blowing performance of the air conditioner.

Although preferred embodiments of the present disclosure have been shown and described herein, the present disclosure is not limited to the specific embodiments described above. It will be understood that various modifications and changes can be made by those skilled in the art without departing from the idea and scope of the present disclosure as defined by the appended claims. Therefore, it shall be considered that such modifications, changes, and equivalents thereof are all included within the scope of the present disclosure.

The invention claimed is:

1. A sterilization device comprising:
   a frame having a first surface and a second surface opposite the first surface, wherein air is introduced through the first surface and discharged through the second surface;
   one or more discharge electrodes disposed within the frame; and
   a plurality of ground electrodes extending in a direction that intersects with a direction extending between the first surface and the second surface,
   wherein the one or more discharge electrodes and the plurality of ground electrodes are alternately arranged,
   wherein each of the one or more discharge electrodes comprises:
      a body extending parallel to the plurality of ground electrodes,
      a first discharge needle protruding from the body toward the first surface, and
      a second discharge needle protruding from the body toward the second surface, and
   wherein the one or more discharge electrodes are inclined with respect to the plurality of ground electrodes.

2. The sterilization device of claim 1, wherein the body has a first bending point curved toward the first surface and a second bending point curved toward the second surface such that the body extends in a zigzag shape.

3. The sterilization device of claim 2, wherein the first discharge needle protrudes from the second bending point, and wherein the second discharge needle protrudes from the first bending point.

4. The sterilization device of claim 2, wherein (i) an imaginary line extending between an end of the first discharge needle and the first bending point and (ii) an imaginary line extending between an end of the second discharge needle and the second bending point are parallel to a longitudinal direction of the body.

5. The sterilization device of claim 1, wherein the body, the first discharge needle, and the second discharge needle are positioned at a same plane.

6. The sterilization device of claim 1, wherein a distance between one of two ground electrodes of the plurality of ground electrodes that is adjacent to the one or more discharge electrodes and an end of the first discharge needle is equal to a distance between the other of the two ground electrodes that is adjacent to the one or more discharge electrodes and an end of the second discharge needle.

7. The sterilization device of claim 1, wherein an angle of each of the one or more discharge electrodes being inclined with respect to the plurality of ground electrodes is in a range of 10° to 20°.

8. The sterilization device of claim 1, wherein a distance between one of two ground electrodes of the plurality of ground electrodes that is adjacent to the one or more discharge electrodes and an end of the first discharge needle, and a distance between the other of the two ground electrodes that is adjacent to the one or more discharge electrodes and an end of the second discharge needle are in a range of 4 mm to 9 mm.

9. The sterilization device of claim 1, wherein the frame comprises a partition wall that divides an interior of the frame into a first sterilization region and a second sterilization region, and
   wherein the one or more discharge electrodes and the plurality of ground electrodes are distributed and disposed between the first sterilization region and the second sterilization region.

10. The sterilization device of claim 9, wherein the first sterilization region and the second sterilization region are symmetrical with respect to the partition wall.

11. The sterilization device of claim 9, wherein the one or more discharge electrodes includes a first discharge electrode and a second discharge electrode,
    wherein the first discharge electrode passes through a center of the partition wall, is disposed above an imaginary center line orthogonal to the partition wall, and is inclined downward toward the second surface, and
    wherein the second discharge electrode is disposed below the imaginary center line and is inclined upward toward the second surface.

12. The sterilization device of claim 9, further comprising:
    a wire configured to apply a voltage to the one or more discharge electrodes; and
    a ground wire connecting the plurality of ground electrodes,
    wherein at least one of the wire or the ground wire is disposed at the partition wall.

13. A sterilization device comprising:
    a frame positioned at an air flow path;
    one or more discharge electrodes disposed within the frame; and
    a plurality of ground electrodes extending in a direction that intersects with an air flow direction along the air flow path,
    wherein the one or more discharge electrodes and the plurality of ground electrodes are alternately arranged,
    wherein each of the one or more discharge electrodes comprises:
       a body extending parallel to the plurality of ground electrodes,
       a first discharge needle protruding from the body toward an upstream of the air flow direction, and
       a second discharge needle protruding from the body toward a downstream of the air flow direction, and
    wherein each of the one or more discharge electrodes is inclined with respect to the plurality of ground electrodes.

14. The sterilization device of claim 13, wherein the frame has a first surface and a second surface opposite the first surface,
    wherein air is introduced through the first surface and discharged through the second surface, and
    wherein the body has a first bending point curved toward the first surface and a second bending point curved toward the second surface such that the body extends in a zigzag shape.

15. The sterilization device of claim 14, wherein the first discharge needle protrudes from the second bending point, and wherein the second discharge needle protrudes from the first bending point.

16. The sterilization device of claim 14, wherein (i) an imaginary line extending between an end of the first discharge needle and the first bending point and (ii) an imaginary line extending between an end of the second discharge needle and the second bending point are parallel to a longitudinal direction of the body.

17. The sterilization device of claim 13, wherein a distance between one of two ground electrodes of the plurality of ground electrodes that is adjacent to the one or more discharge electrodes and an end of the first discharge needle is equal to a distance between the other of the two ground electrodes that is adjacent to the one or more discharge electrodes and an end of the second discharge needle.

18. The sterilization device of claim 13, wherein an angle of each of the one or more discharge electrodes being inclined with respect to the plurality of ground electrodes is in a range of 10° to 20°.

19. The sterilization device of claim 13, wherein a distance between one of two ground electrodes of the plurality of ground electrodes that is adjacent to the one or more discharge electrodes and an end of the first discharge needle, and a distance between the other of the two ground electrodes that is adjacent to the one or more discharge electrodes and an end of the second discharge needle are in a range of 4 mm to 9 mm.

20. The sterilization device of claim 13, wherein the frame comprises a partition wall that divides an interior of the frame into a first sterilization region and a second sterilization region, and
    wherein the one or more discharge electrodes and the plurality of ground electrodes are distributed and disposed between the first sterilization region and the second sterilization region.

21. The sterilization device of claim 13, wherein the body, the first discharge needle, and the second discharge needle are positioned at a same plane.

\* \* \* \* \*